(12) United States Patent
Florent et al.

(10) Patent No.: US 7,289,652 B2
(45) Date of Patent: *Oct. 30, 2007

(54) MEDICAL VIEWING SYSTEM AND METHOD FOR DETECTING AND ENHANCING STRUCTURES IN NOISY IMAGES

(75) Inventors: Raoul Florent, Ville d'Avray (FR); Lucile Nosjean, Rueil-Malmaison (FR); Pierre Lelong, Nogent sur Marne (FR)

(73) Assignee: Koninklijke Philips Electronics, N. V., Eindhoven (NL)

( * ) Notice: Subject to any disclaimer, the term of this patent is extended or adjusted under 35 U.S.C. 154(b) by 603 days.

This patent is subject to a terminal disclaimer.

(21) Appl. No.: 10/496,450

(22) PCT Filed: Nov. 4, 2002

(86) PCT No.: PCT/IB02/04600

§ 371 (c)(1),
(2), (4) Date: May 21, 2004

(87) PCT Pub. No.: WO03/043516

PCT Pub. Date: May 30, 2003

(65) Prior Publication Data

US 2004/0260175 A1 Dec. 23, 2004

(30) Foreign Application Priority Data

Nov. 21, 2001 (EP) .................................. 01402987

(51) Int. Cl.
*G06K 9/00* (2006.01)

(52) U.S. Cl. .................................................. 382/130

(58) Field of Classification Search ................ 382/294, 382/287, 130, 100, 128; 623/1.11; 606/7
See application file for complete search history.

(56) References Cited

U.S. PATENT DOCUMENTS 4,762,129 A * 8/1988 Bonzel ........................ 606/194

(Continued)

FOREIGN PATENT DOCUMENTS

EP 1057455 A2 * 12/2000

OTHER PUBLICATIONS

Improved Image Guidance of Coronary Stent Deployment☐☐Robert A. Close, Craig K. Abbey and James S. Whiting☐☐Proceedings of SPIE vol. 3976 (2000).*
Decomposition of Coronary Angiograms into Non-Rigid Nmoving Layers☐☐R.A. Close and J.S. Whiting☐☐SPIE vol. 3661, Feb. 1999.*

(Continued)

*Primary Examiner*—Vikkram Bali

(57) ABSTRACT

A medical viewing system for displaying a sequence of images of a medical intervention that comprises moving and/or positioning a tool in a body organ, which tool is carried by a support to which at least one marker is attached at a predetermined location with respect to the tool, comprising means for acquiring the sequence of images, and for processing said images during the medical intervention, wherein: extracting means for automatically extracting at least one marker that is attached to the tool support and that neither belongs to the tool nor to the body organ, and yielding the marker location information; computing means for automatically deriving the tool location information from the marker location information, and enhancing means for improving the visibility of the tool and/or the body organ in order to check whether the medical intervention stages are successfully carried out.

16 Claims, 4 Drawing Sheets

U.S. PATENT DOCUMENTS

| | | | | |
|---|---|---|---|---|
| 5,209,728 A | * | 5/1993 | Kraus et al. | 604/96.01 |
| 5,293,574 A | * | 3/1994 | Roehm et al. | 378/98.2 |
| 5,467,380 A | * | 11/1995 | De Jonge et al. | 378/98.2 |
| 5,771,895 A | * | 6/1998 | Slager | 600/462 |
| 5,803,914 A | * | 9/1998 | Ryals et al. | 600/407 |
| 6,117,101 A | * | 9/2000 | Diederich et al. | 604/22 |
| 6,532,380 B1 | * | 3/2003 | Close et al. | 600/431 |

OTHER PUBLICATIONS

John C. Russ Image Processing Handbook, 3RD Edition (1999) CRC Press LLC.*

Layer Decomposition of Coronary Angiograms Medical Imaging 2000:Image Processing SPIE vol. 3979(2000).*

Kompatsiaris, et al.; Deformable Boundary Detection of Stents in Angiographic Imgaes; IEEE, vol. 19, Jun. 2000; pp. 652-662.

* cited by examiner

MEDICAL VIEWING SYSTEM AND METHOD FOR DETECTING AND ENHANCING STRUCTURES IN NOISY IMAGES

FIELD OF THE INVENTION

The invention relates to a medical viewing system for displaying a sequence of images of a medical intervention that comprises moving and/or positioning a tool in a body organ. The invention also relates to a computer executable image processing method to be used in said system. The invention further relates to a medical examination apparatus coupled to such a system. The invention finds for example its application in the medical field of cardiology, for extracting, registering and enhancing thin objects of interest such as stents and vessel walls in arteriograms.

BACKGROUND OF THE INVENTION

A method for extracting stents in medical images is already known from the publication entitled "Deformable Boundary Detection of Stents in Angiographic Images", by Ioannis Kompatsiaris et alii, in IEEE TRANSACTIONS ON MEDICAL IMAGING, VOL.19, No. 6, JUNE 2000, pages 652-662. This document describes an image processing method for deformable boundary detection of medical tools, called stents, in angiographic images. A stent is a surgical stainless steel coil that is placed in the artery in order to improve blood circulation in regions where a stenosis has appeared. Assuming initially a set of three-dimensional (3-D) models of stents and using perspective projection of various deformations of the 3-D model of the stent, a large set of two-dimensional (2-D) images of stents is constructed. These synthetic images are then used as a training set for deriving a multi-variate density estimate based on eigenspace decomposition and formulating a maximum-likelihood estimation framework in order to reach an initial rough estimate for automatic object recognition. The silhouette of the detected stent is then refined by using a 2-D active contour (snake) algorithm, integrated with an iterative initialization technique, which takes into consideration the geometry of the stent.

As disclosed in the cited publication, when a narrowing called stenosis is identified in a coronary artery of a patient, a procedure called angioplasty may be prescribed to improve blood flow to the heart muscle by opening the blockage. In recent years, angioplasty increasingly employs a stent implantation technique. This stent implantation technique includes an operation of stent placement at the location of the detected stenosis in order to efficiently hold open the diseased vessel, as illustrated by FIG. 2 of the cited publication. Stent placement helps many patients to avoid emergency heart bypass surgery and/or heart attack (myocardial infraction). The stent, as illustrated by FIG. 1 of the cited publication, is a small, slotted, stainless steel tube cut by a precision laser for forming a coil. It is wrapped tightly around a balloon attached to a monorail introduced by way of a catheter and a guide-wire forming a device called balloon-tipped catheter. This balloon-tipped catheter is introduced into the artery through a small incision. Once in place, the balloon is inflated in order to expand the coil. Once expanded, the stent, which can be considered as a permanent implant, acts like a scaffold keeping the artery wall open. This allows more blood flow to the heart muscle.

SUMMARY OF THE INVENTION

The stent, the monorail and the thin guide-wire are observed in noisy fluoroscopic images. They show low radiographic contrast that makes evaluation of the placement and expansion of said stents at an accurate location very difficult. Also, during the operation of stent implantation, the monorail, with the balloon and stent wrapped around it, is moving with respect to the artery, the artery is moving under the influence of the cardiac pulses, and said artery is seen on a background that is moving under the influence of the patient's breathing. These movements make the following of stent implantation under fluoroscopic imaging still more difficult to visualize. In particular, these movements make zooming inefficient because the object of interest may get out of the zoomed image frame. Clinical problems are associated with inadequate expansion of the stent, improper placement of the stent, and gap or overlap between several stents. Studies revealed that more than eighty per cent of stents might be insufficiently dilated despite an apparently angiographically successful deployment. Inadequately expanded stents can locally disrupt blood flow and cause thrombosis.

The method that is disclosed in the cited publication deeply relies on the identification of the stent in the angiographic images. This known method has steps of forming sets of 3-D models of stents, steps of constructing sets of 2-D images from the 3-D models and steps of matching the 2-D models to the 2-D images of the stent in the cardiograms. This method would present a calculation load that is actually too heavy for real time processing of a sequence of images needed in the intervention phase of stent implantation. Also, the practitioners are more and more demanding about the resolution of the images. So, the proposed method may be preferably only used in a post-intervention phase.

Instead, it is an object of the invention to propose a medical viewing system that has means to process medical images in order to be used during the intervention phase. For visualizing the intervention of stent implantation, this system has means to solve the problems of automatically extracting features that permits of accurately positioning a balloon with respect to the stenosed zone of the artery, for example for inflating the balloon so as to expand the lumen of the artery, instead of, or before expanding a stent; and automatically extracting features that permit of accurately positioning a balloon, with a stent wrapped around it, for expanding the stent.

According to the invention, these problems are not solved by merely extracting the stent or the artery walls. Instead, these problems are solved by extracting features that do not belong to the objects to be actually finally of interest for the practitioner such as stent or artery walls. As a matter of fact, as explained above, said objects are by nature badly contrasted, represented on an already noisy background and submitted to motions. According to the invention, a medical viewing system is provided comprising means for acquiring a sequence of images, and for processing and displaying said images during the medical intervention, wherein means for automatically extracting at least one marker that is attached to the tool support and that neither belongs to the tool nor to the body organ, and for yielding the marker location information, means for automatically deriving the tool location information from the marker location information, and means for improving the visibility of the tool and/or the body organ in order to check whether the medical intervention stages are successfully carried out. It is also an object of the invention to provide such a system whose image processing means is user-actuatable. It is a further object of the invention to propose such a viewing system, wherein the processing means comprises registering means, enhancing means and zooming means that permit of accurately visualizing the artery walls at the stenosis location; and/or checking stent deployment with respect to the artery walls in regions of interest.

Such a system is claimed in Claim 1 and in dependent Claims. An image processing method to be used in the system, a program product to implement the steps of the method of the invention and an examination apparatus for helping visualization of interventions having such a system are further claimed.

In an application to angioplasty, the system comprises means to extract features not belonging to the stent or to the artery, among which a feature called guide-wire tip located at the extremity of the guide-wire guiding the monorail; and/or at least one feature called balloon-marker located on the monorail at a given position with respect to the balloon; preferably there are two balloon markers disposed at each extremity of the balloon. The guide-wire tip belongs neither to the artery walls nor to the stent, since it belongs to the guide-wire. Also, the balloon-markers belong neither to the vessel walls nor to the stent since they belong to said monorail. Using the method of the invention, the guide-wire tip and the balloon-markers are accurately detected and this detection further permits of accurately localizing the stenosed artery walls and the stent. Advantages of the system and method of the invention are that they improve the results of the intervention phase of stent implantation in a way that is precise and robust; they provide accurate stenosis detection and stent deployment checking during the intervention phase or in a post-intervention phase.

LIST OF DRAWINGS

Embodiments of the invention are described hereafter in detail in reference to diagrammatic figures wherein.

DESCRIPTION OF EMBODIMENTS

The invention relates to a viewing system, and to a computer executable image processing method that is used in the viewing system, for detecting, localizing, registering, enhancing and zooming structures in noisy images. The viewing system and the image processing method of the invention are described hereafter in an example of application to the medical field of cardiology. In said application, the objects of interest are organs such as arteries and tools such as balloons or stents. They are observed during a medical intervention called angioplasty, in a sequence of X-ray fluoroscopic images called angiograms. The system and method may be applied to other tools than stents and balloon in other intervention than angioplasty. For instance, the objects of interest may be electrodes and the organ may be the brain.

Figure 2:
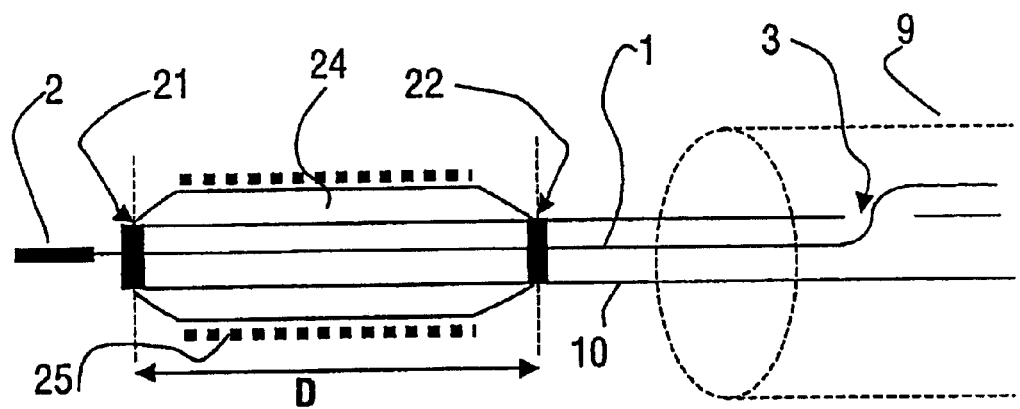
FIG. 2 illustrates the device constituted by a catheter, a guide-wire and a monorail with a balloon and a stent wrapped around it.
Figure 3A:
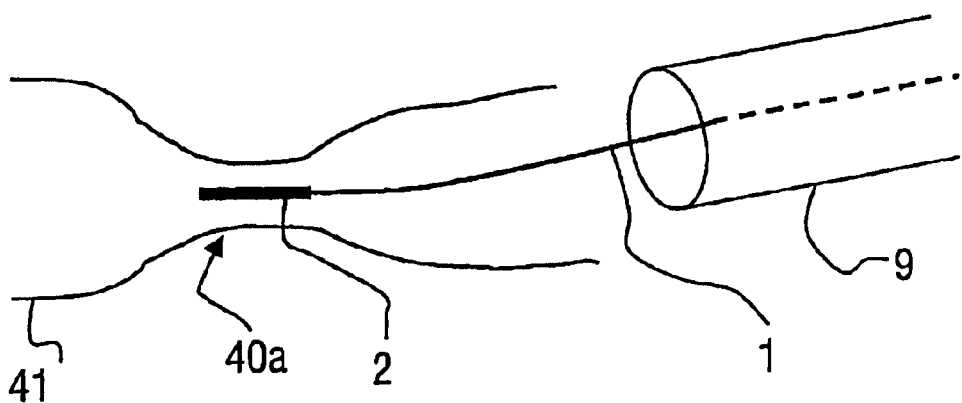
FIG. 3A to FIG. 3F illustrate the information obtained during the intervention stages of angioplasty using the system of the invention.
Figure 3B:
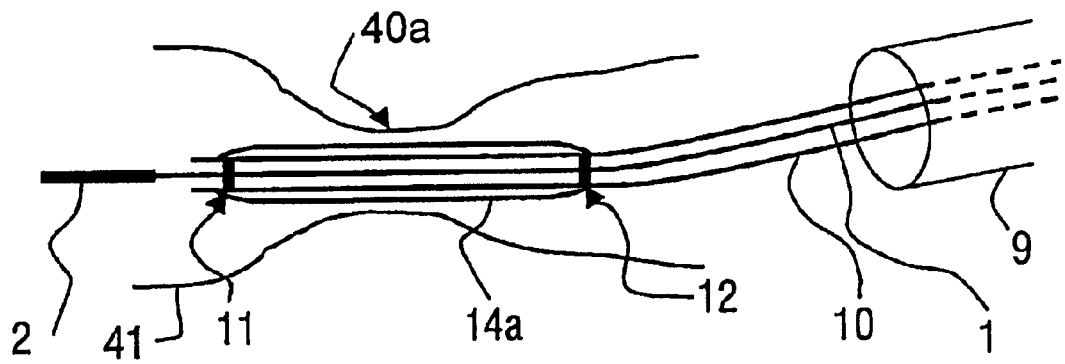
Figure 3C:
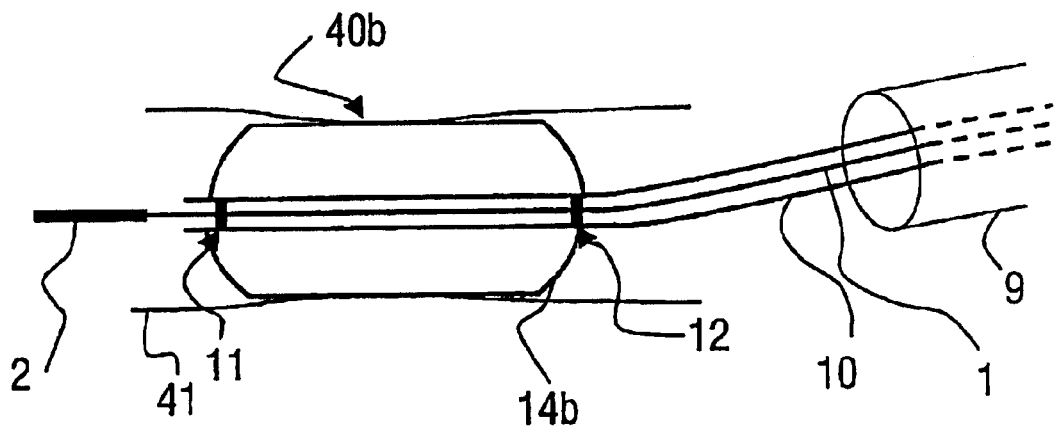
Figure 3D:
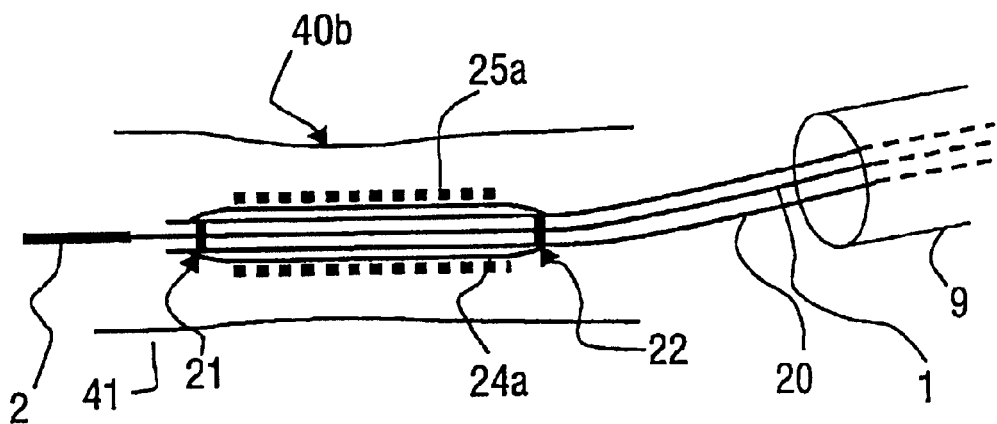
Figure 3E:
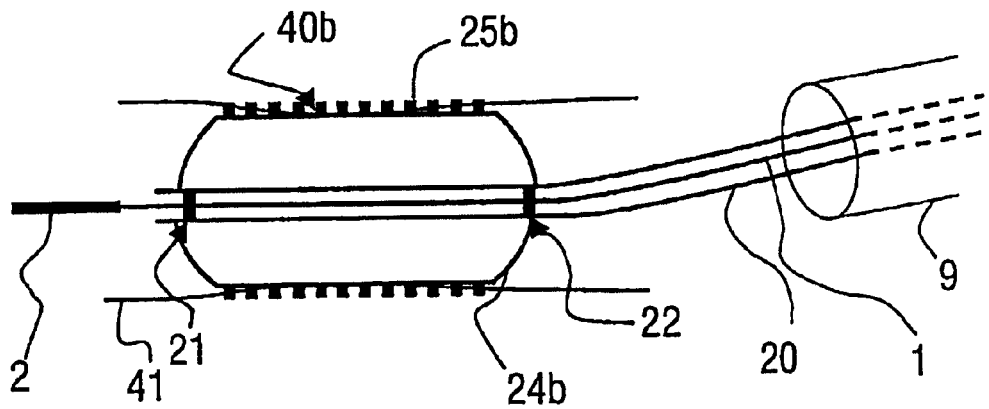
Figure 3F:
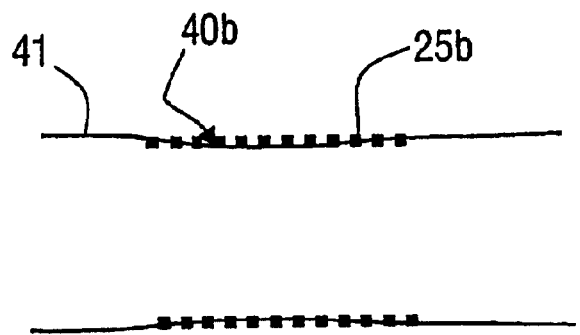

The stent implantation is a medical intervention that usually comprises several stages for enlarging an artery at the location of a lesion called stenosis. In a preliminary stage, the practitioner localizes a stenosis 40a in a patient's artery 41 as best as possible in medical images. This medical intervention includes stages of:

a) Referring to FIG. 3A, introduction in the artery 41, using a catheter 9, of a thin guide-wire 1 that extends beyond the extremity of the catheter 9, and passes through the small lumen of the artery portion 40a at the location of the stenosis.

b) Referring to FIG. 3B, introduction of a monorail 10, which is guided by said guide-wire 1 that passes through the opening 3 of the monorail 10 as illustrated by FIG. 2, and which has a first balloon 14a wrapped around its extremity, without stent; and positioning said first balloon 14a in the artery portion 40a at the stenosis location.

c) Referring to FIG. 3C, inflation of this first balloon 14a, which becomes the inflated balloon 14b, for expanding the narrow lumen 40a of the artery 41 at the location of the stenosis to become the enlarged portion 40b of the artery; then, removal of the first balloon 14b with the first monorail 10.

d) Referring to FIG. 3D, again using the catheter 9 and the thin guide-wire 1, introduction of a second monorail 20 with a second balloon 24a wrapped around its extremity, and with a stent 25a around said second balloon 24a; and positioning said second balloon with the stent at the location of the stenosis in the previously expanded lumen 40b of the artery 41.

e) Referring to FIG. 3E, inflation of the second balloon 24a to become the inflated balloon 24b in order to expand the coil forming the stent 25a, which becomes the expanded stent 25b embedded in the artery wall.

f) Referring to FIG. 3F, considering the expanded stent 25b as a permanent implant, removing the second balloon 24b, the second monorail 20, the guide-wire 1 and catheter 9.

The medical intervention called angioplasty is difficult to carry out due to badly contrasted medical images, where the guide-wire, balloon, stent and vessel walls are hardly distinguishable on a noisy background and are moreover submitted to motions. Some phases of this intervention are very critical, so checking actions have to be performed during these phases. These phases are:

Phase 1) after stage a) it is important to check the position of the guide-wire 1 with respect to an artery portion of interest 40a, such as the stenosed zone.

Phase 2) between stages b) and c), it is important to check whether the first balloon 14a is placed correctly in coincidence with the stenosed zone 40a of the artery 41.

Phase 3) after stage c), it is important to inspect the artery portion in order to verify the removal of the stenosis by the previous expansion of the first balloon.

Phase 4) between stages d) and e), it is critical to check whether the stent 25a is accurately positioned with respect to the expanded lumen 40b of the artery 41.

Phase 5) After stage e) it is very important to check whether the balloon 24b is sufficiently inflated, and whether the stent 25b is successfully expanded in the artery to be embedded in the artery wall, in order to gauge the result of the operation.

Phase 6) after stage f), it is important to be able to perform checking of the condition of the stent 25b after implantation in the artery portion.

The system of the invention has means to perform these actions during the intervention at the above-cited critical phases. The user is the actor of the medical intervention and can have the possibility to intervene at each phase. First of all, the user might choose a region of interest in the images. Besides, the user has at his disposal control means 58, shown in FIG. 5, to activate and control the image processing means. These control means comprises starting means and stopping means for the user to start the processing operation, to control the duration of the processing operation and to end the processing operation. The processing means are actuated by the user during one of the. above-cited phases, for example while not moving the tool or tools.

Figure 1:
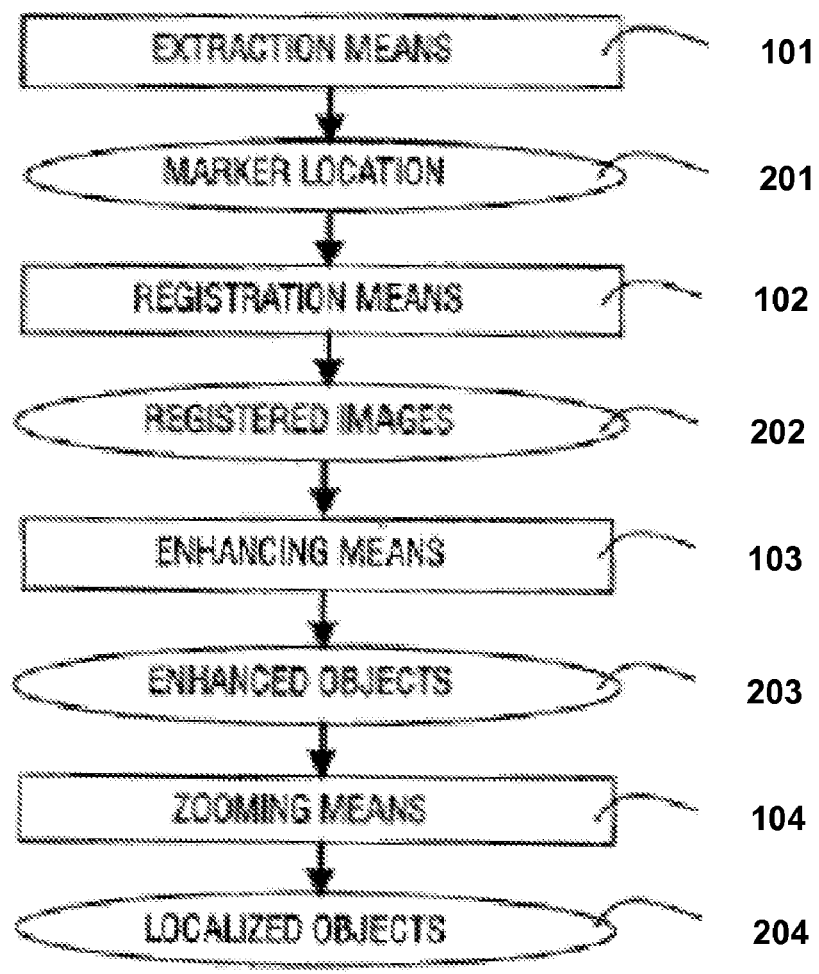
FIG. 1 is a functional block diagram of means of the system.

Referring to FIG. 1, these image processing means include extracting means 101 that solves the problems of automatically and accurately localizing specific features in the sequence. Once the specific feature location 201 has been determined by the automatic extracting means 101, registering means 102 provides registered sequence images 202, based on the specific feature location 201. Then, enhancing means 103 yields images 203 with enhanced objects of interest, such as the tool and/or the artery walls. Zooming means 104, that are now applied to stable objects of interest in the registered images, permits an improved visualization of the regions of interest with the tools and the blood vessels in processed images 204.

The processed images permit of checking the position of the guide-wire with respect to the stenosed zone of the artery; of checking the position of the first balloon with respect to the stenosed zone before expanding the lumen of the artery; permits of checking the position of the second balloon, with the stent wrapped around it, before stent expansion and permits of finally checking the expanded stent.

According to the invention, these specific features are not merely the stent or the artery walls. Instead, these specific features do not belong to the badly contrasted stent or vessel walls, which are the objects that are actually finally of interest for the practitioner. According to the invention, the system has extracting means 101 to automatically and accurately extract specific features among which a feature called guide-wire tip 2 located at the extremity of the thin guide-wire 1 guiding the monorail 10 or 20; and/or at least one feature called balloon-marker 11, 12 or 21, 22 located respectively on the monorail 10, 20 at a given position with respect to the balloon respectively 14a, 24a; preferably there are two balloon-markers disposed at each extremity of the balloon. The guide-wire tip 2 belongs neither to the artery walls 41 nor to the stent 25a, since it belongs to the guide-wire 1. Also, the balloon-markers 11, 12 or 21, 22 belong neither to the vessel walls 41 nor to the stent 25a since they belong to the monorail 10 or 20. These markers have a specific easily recognizable shape, and are made of a material highly contrasted in the images. Hence they are easy to extract. The system processing means 102, 103, 104 permit of accurately deriving the location of the balloons 14a, 24a, 14b, 24b, since the balloons have specific locations with respect to the balloon-markers. Also, the stents 25a, 25b are accurately localized, since the stents have specific locations with respect to the balloon-markers though said stents are not attached to said balloon-markers. The automatic location of said markers permits of performing the actions required at phases 1), 2), and 4). Moreover, the system processing means permit of automatically and accurately detect specific features such as boundaries of the previously localized artery walls and stent. The result of these image processing steps further permits of checking the proper expansion of the lumen of the artery after the inflation of the first balloon; and permits of checking the proper expansion of the stent after the inflation of the second balloon. Hence, the result of these image processing operations permits of performing the actions required at phases 3), 5), and 6).

Figure 4:
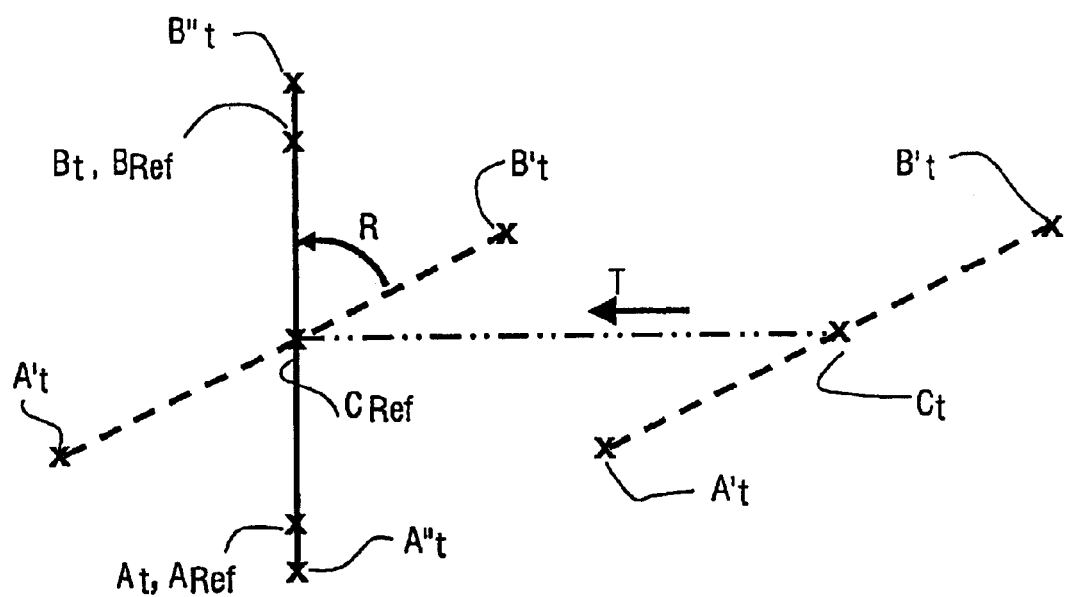
FIG. 4 illustrates the step of marker registration.

Referring to FIG. 4, for instance two markers $A_{Ref}$, $B_{Ref}$ have been detected in an image of the sequence, called image of reference, which may be the image at starting time. The markers $A_{Ref}$, $B_{Ref}$ may be selected by automatic means. They are extracted using extracting means 101 of the system. Then, registering means 102 of the system, using the marker location information $A_{Ref}$, $B_{Ref}$ in the reference image and corresponding extracted markers $A'_t$, $B'_t$ in a current image of the sequence, are operated for automatically registering the current image on the reference image. This operation is performed by matching the markers of the current image to the corresponding markers of the reference image, comprising possible geometrical operations including: A translation T to match a centroid $C_t$ of the segment $A'_t$ $B'_t$ of the current image with a centroid $C_{Ref}$ of the segment $A_{Ref} B_{Ref}$ of the reference image; a rotation R to match the direction of the segment $A'_t$, $B'_t$ of the current image with the direction of the segment $A_{Ref}$ $B_{Ref}$ of the reference image, resulting in a segment $A''_t$, $B''_t$; and a dilation A for matching the length of the resulting segment $A''_t$, $B''_t$ with the length of the segment $A_{Ref} B_{Ref}$ of the reference image, resulting in the registered segment $A_t$, $B_t$ for the registered current image. Such operations of translation T, rotation R and dilation $\Delta$ are defined between the images of the sequence and the reference image, resulting in the registration of the whole sequence. This operation of registration is not necessarily performed on all the points of the images. Zones of interest comprising the markers may be delimited. This operation of registration permits of minimizing the effect of respective movements of the objects of interest, such as vessels, guide-wire, balloons and stent, with respect to a predetermined image referential. In the registered images, the user can easily perform zooming Z on objects of interest. Preferably, two markers, or more, are used for better registration.

In the registered sequence, an object of interest, such as stent, can be enhanced by the enhancing means 103. For this operation, the shape and dimension of the stent is a-priori knowledge that can be stored in memory means of the system. The boundaries of the stent are substantially parallel to the segment formed by the balloon-markers, and at a distance from this segment that can be derived from the a-priori knowledge. So, these boundaries are detected, extracted and enhanced by the enhancing means 103 of the system. Also, the artery walls can be detected, extracted and enhanced by the enhancing means 103 in a similar manner.

The registered images are preferably filtered for minimizing noise. The system enhancing means 103 may comprise noise filter means. In an example, the registered images are integrated by averaging means applied to the intensity of the points. By this operation, the details of objects, such as vessels, which are in time concordance, are enhanced while the details of the background, which are not in time concordance, are minimized. The registered images are also preferably submitted to spatial background subtraction means of the enhancing means 103. Background subtraction means permits of eliminating large contrasted zones and permits of again enhancing the objects of interest.

A computer executable image processing method to be used in a system as above described has steps of processing a sequence of digital images during the medical intervention, comprising automatically extracting at least a marker that belongs neither to the tool nor to the body organ, automatically determining the marker location information in the images of the sequence, deriving the tool location information from the marker location information, and processing the images to improve the visibility of the tool and/or of the organ. The method permits of displaying the images during the medical intervention for the user to position the tool in the organ at a specific location using the marker location information.

Figure 5:
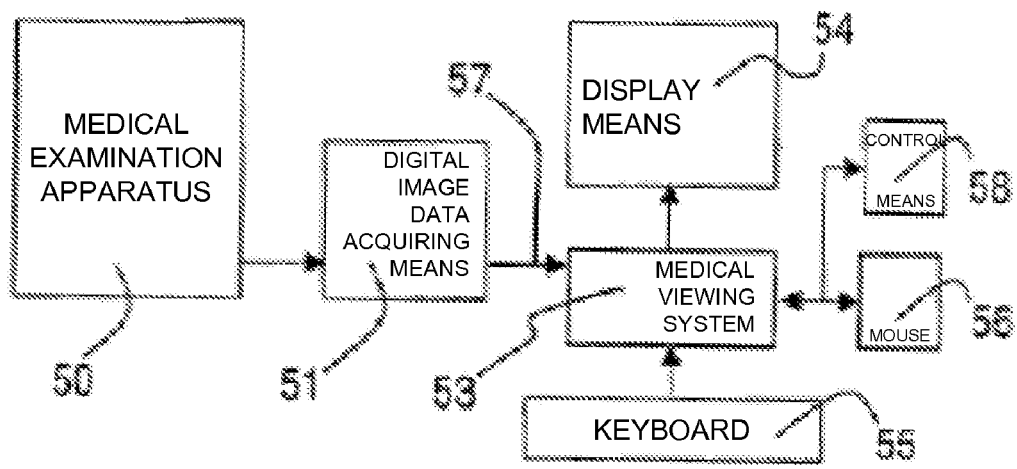
FIG. 5 is a functional block diagram of a medical examination apparatus using said system.

FIG. 5 shows a diagram of a medical examination apparatus 50. The apparatus has means 51 for acquiring digital image data of a sequence of images, and is coupled to a medical viewing system 53 as described above, for processing these data according to the processing method cited above. The medical viewing system is generally used in the intervention room or near the intervention room for processing real time images. Steps of the present method can be applied on stored medical images, for example for estimating medical parameters. The system for processing the data of the stored images is then called medical viewing station. The medical examination apparatus provides the image data by connection 57 to the system 53. The system provides processed image data to display means and/or storage means. The display means 54 may be a screen. The storage means may be a memory MEM of the system 53. Said storage means may be alternately external storage means. This image viewing system 53 may comprise a suitably programmed computer, or a special purpose processor having circuit means such as LUTs, Memories, Filters, Logic Operators, that are arranged to perform the functions of the method steps according to the invention. The system 53 may also comprise a keyboard 55 and a mouse 56. Icones may be provided on the screen to be activated by mouse-clicks, or special pushbuttons may be provided on the system, to constitute control means 58 for the user to start, to control the duration or to stop the processing means of the system at chosen stages or phases.

The invention claimed is:

1. A medical viewing system for displaying a sequence of images of a medical intervention that comprises positioning a tool in a body organ, the tool configured to be carried by a support, wherein the support includes at least one localizing feature marker at a predetermined location with respect to the tool, comprising:
   acquisition means for acquiring the sequence of images;
   processing means for processing said images of the sequence of images;
   extraction means for extracting information from said images related to the at least one localizing feature marker of the support and for use in computing marker location information;
   computer means for calculating tool location information as a function of the marker location information; and
   enhancement means for enhancing a visibility of the tool and the body organ within the displayed sequence of images as a function of the calculated tool location information.

2. The system of claim 1, further comprising controller means to direct the processing means in connection with a selected stage of the medical intervention.

3. The system of claim 1, wherein the computer means further comprises:
   selection means for selecting a reference image of the sequence and at least one reference marker in the reference image; and
   registration means configured to use marker location information extracted from (i) the reference image and (ii) a current image of the sequence, for registering the current image of the sequence on the reference image by matching the extracted marker of the current image to the reference marker of the reference image.

4. The system of claim 1, wherein the enhancement means further comprises:
   storage means for storing information related to dimensions of the tool or the body organ; and
   computer means, configured to use the marker location information and the information related to dimensions of the tool or the body organ, to extract and enhance image features of the tool or the body organ within the displayed sequence of images.

5. The system of claim 4, wherein the enhancement means for enhancing further comprises:
   zoom means for zooming on a region of interest within the displayed sequence of images;
   noise filter means for filtering noise as part of enhancing objects of interest within the displayed sequence of images; and
   background subtraction means for subtracting background from the displayed sequence of images.

6. The medical viewing system of claim 1, wherein
   the tool includes a balloon carried by a monorail support, said support including two attached localizing balloon markers;
   the extraction means determines balloon marker location information;
   the computer means derives balloon location information at least in part from the balloon marker location information and the enhancement means improves the visibility of the balloon or the area in the vicinity of the balloon; and further comprising:
   a display means for displaying the images during the intervention.

7. The system of claim 6, further comprising
   a guide wire for guiding the monorail, said guide wire having a tip including a tip marker for localizing; and wherein
   the extraction means further determines tip marker location information.

8. The system of claim 7, wherein
   the tool further includes a stent wrapped around the balloon; and
   the computer means calculates stent location information based at least in part on the balloon marker location information.

9. The system of claim 6, further comprising:
   activation means for the user to activate or stop, at a selected stage of the medical intervention, the processing means applied to the sequence of images for improving the visibility of the tool or the body organ, said selected stage including at least one stage chosen from among a group of stages consisting of
   positioning the guide wire tip with respect to an artery portion;
   positioning the balloon markers with respect to the location of the portion of the artery, before a stage of balloon inflation or a stage of stent deployment; and
   inspection of the artery portion after the stage of balloon inflation or the stage of stent deployment.

10. The system of claim 6, wherein the computer means further comprises:
   selection means for selecting a reference image and location means for calculating information related to locations of the balloon markers in the reference image; and
   registration means for using the balloon marker location information in the reference image and in other images of the sequence for registering the images of the sequence by matching corresponding balloon markers of a current image to balloon markers of the reference image.

11. The system of claim 10, wherein the enhancement means further comprises:

storage means for storing previously gathered information related to at least one item selected from the group consisting of the balloon, a stent associated with the balloon, an area surrounding the balloon, and an area surrounding the stent, wherein said computer means uses the balloon marker location information and the previously gathered information for localizing the at least one item, and wherein said enhancing means enhances the visibility of the at least one item within the displayed images as a function of the localizing of the at least one item.

12. An image processing method for visualizing a medical intervention that includes positioning a tool in a body organ, comprising the steps of:

acquiring a sequence of images during the medical intervention; and processing said images during the medical intervention, wherein the processing includes extracting from each image a marker, wherein the marker belongs neither to the tool nor to the body organ, computing marker location information of respective markers in the images of the sequence, computing tool location information from the marker location information, and enhancing the images as a function of the computed tool location information to improve the visibility of the tool within the enhanced images; and displaying the enhanced images during the medical intervention.

13. The method of claim 12, wherein the processing step further comprises at least one step selected from the group consisting of registering the images of the sequence on a reference image;

filtering noise in the images;

subtracting background from the images; and zooming objects of interest in the images.

14. A computer-readable medium containing machine-readable instructions executable by a computer for carrying out the method of claim 12.

15. A computer-readable medium containing machine-readable instructions executable by a computer for carrying out the method of claim 13.

16. The method of claim 12, wherein the images of the sequence comprise angiograms.

* * * * *